US009404856B2

United States Patent
Li et al.

(10) Patent No.: US 9,404,856 B2
(45) Date of Patent: Aug. 2, 2016

(54) OPTICAL REFRACTIVE INDEX MEASURING SYSTEM BASED ON SPECKLE CORRELATION

(71) Applicant: Macau University of Science and Technology, Taipa (MO)

(72) Inventors: Jianqing Li, Taipa (MO); Ben Xu, Taipa (MO); Yuanyuan Pan, Taipa (MO)

(73) Assignee: Macau University of Science and Technology, Macau (CN)

( * ) Notice: Subject to any disclaimer, the term of this patent is extended or adjusted under 35 U.S.C. 154(b) by 467 days.

(21) Appl. No.: 13/907,993

(22) Filed: Jun. 3, 2013

(65) Prior Publication Data

US 2014/0354979 A1    Dec. 4, 2014

(51) Int. Cl.
*G01N 21/41* (2006.01)
*G01N 21/43* (2006.01)

(52) U.S. Cl.
CPC .......... *G01N 21/41* (2013.01); *G01N 2021/433* (2013.01); *G01N 2021/438* (2013.01)

(58) Field of Classification Search
CPC ............ G01N 21/41; G01N 2021/438; G01N 2021/433
USPC ......................................................... 356/128
See application file for complete search history.

(56) References Cited

U.S. PATENT DOCUMENTS 4,981,338 A * 1/1991 Bobb et al. ...................... 385/12
5,600,433 A * 2/1997 Buttry et al. ................... 356/128

OTHER PUBLICATIONS

Donlagic, Denis and Miha Zavrsnik, "Fiber optic microbend sensor structure", Jun. 1, 1997, vol. 22, No. 11, Optics Letters, p. 837-839.*
Fujiwara, Eric, Yu Tzu Wu, Carlos Kenichi Suzuki, "Vibration based specklegram fiber sensor for measurement of properties of liquids," Optics and Lasers in Engineering, 50 (2012), pp. 1726-1730.*
Biazoli, Claudecir R., et al. "Multimode interference tapered fiber refractive index sensors." Applied optics 51.24 (2012): 5941-5945.*

* cited by examiner

*Primary Examiner* — Rebecca C Bryant
(74) *Attorney, Agent, or Firm* — Eagle IP Limited; Jacqueline C. Lui

(57) ABSTRACT

An optical detection system for measuring a refractive index of a liquid analyte comprising a light transmitting assembly fiber, which includes a single-mode fiber, an optical fiber sensing module and a multi-mode fiber. The optical detection system is configured to emit a coherent light beam to one end of the assembly fiber; and a detector is configured to capture a specklegram from an exit end of the assembly fiber. When the optical detection system is in operation, the optical fiber sensing module is configured to be submerged into the liquid analyte. By analyzing the correlation between the specklegram corresponding to the liquid analyte and the reference specklegram, the refractive index of the liquid analyte can be obtained.

18 Claims, 5 Drawing Sheets

OPTICAL REFRACTIVE INDEX MEASURING SYSTEM BASED ON SPECKLE CORRELATION

FIELD OF INVENTION

This invention relates to a refractive index (RI) measuring system, and in particular a refractive index measuring system utilizing a refractive index sensing module and specklegram to measure refractive index based on speckle correlation.

BACKGROUND OF INVENTION

There are a number of ways to implement refractive index sensing, which include using a fiber Bragg grating (FBG), long period grating (LPG), macro-bend single-mode fiber (SMF), surface plasmon resonance (SPR), a Fabry-Perot interferometer (FPI), a multi-D-shaped optical fiber or a single-mode-multimode-single-mode (SMS) fiber structure. For these sensors, the RI information is extracted by measuring the RI-induced shift in the peak wavelength of these sensors' spectrum, which involves a complex and expensive system.

SUMMARY OF INVENTION

In the light of the foregoing background, it is an object of the present invention to provide an alternate, a simple yet low-cost optical refractive index measuring system. In particular, the present invention discloses an optical refractive index measuring system utilizing a refractive index sensing module and specklegram to measure refractive index based on speckle correlation.

Accordingly, the present invention, in one aspect, is an optical detection system for measuring a refractive index of a liquid analyte comprising a light transmitting assembly fiber, which includes a single-mode fiber, a no-core optical fiber sensing module and a multi-mode fiber, wherein the no-core optical fiber sensing module is sandwiched between the single-mode fiber and the multi-mode fiber; a coherent light source is configured to emit a coherent light beam to a first end of said assembly fiber located at the single-mode fiber; and a detector is configured to capture a signal from a second end of the assembly fiber located at the multi-mode fiber. When the optical detection system is in operation, the no-core optical fiber sensing module is configured to be submerged into the liquid analyte.

In an exemplary embodiment of the present invention, the no-core optical fiber sensing module in the optical detection system comprises a first section and a second section; the diameter of the no-core optical fiber sensing module being continuously decreasing along the longitude axis in the first section and continuously increasing along the longitude axis of the second region; and the diameter of the first and second end of the no-core optical fiber sensing module being equal to the diameters of the single-mode fiber and the multi-mode fiber respectively. In another embodiment, the no-core optical fiber sensing module is biconical shaped.

In another embodiment, the detector is an image sensor. In yet another embodiment, the single-mode fiber is a polarization-maintaining single-mode fiber.

According to another aspect of the present invention, a method of measuring refractive index of a liquid analyte is disclosed. The method comprises the steps of providing a light transmitting assembly fiber comprising a no-core optical fiber sensing module, a single mode fiber and a multi-mode fiber, wherein the no-core optical fiber sensing module is sandwiched between the single-mode fiber and the multi-mode fiber; disposing the no-core optical fiber sensing module into the liquid analyte; irradiating a coherent light beam to a first end of the assembly fiber located at the single-mode fiber by a coherent light source; capturing a signal at a second end of the assembly fiber located at the multi-mode fiber by a detector; and determining the refractive index of the liquid analyte based on the captured signal.

In an embodiment, the signal is in a form of specklegram. In another embodiment, the step of determining a refractive index of the liquid by analyzing the correlation between the captured specklegram signal and a reference specklegram signal through a correlation function. In yet another embodiment, the correlation function is $$r = \frac{\sum_m \sum_n (A_{mn} - \overline{A})(B_{mn} - \overline{B})}{\sqrt{\left(\sum_m \sum_n (A_{mn} - \overline{A})^2\right)\left(\sum_m \sum_n (B_{mn} - \overline{B})^2\right)}}$$

where A is the captured specklegram signal and B is the reference specklegram signal stored in the computer-readable storage medium; m and n are the coordinates of a pixel of the specklegram; $A_{mn}$ and $B_{mn}$ denote the intensity of pixel (m, n) in A and B; and $\overline{A}$ and $\overline{B}$ are the average intensity of all the pixels in A and B.

There are many advantages to the present invention. In particular, the present invention provides a simple intensity-based optical fiber refractive index measuring system with high sensitivity, low manufacturing difficulties and low manufacturing cost.

DETAILED DESCRIPTION OF THE PREFERRED EMBODIMENTS

As used herein and in the claims, "comprising" means including the following elements but not excluding others.

Figure 1:
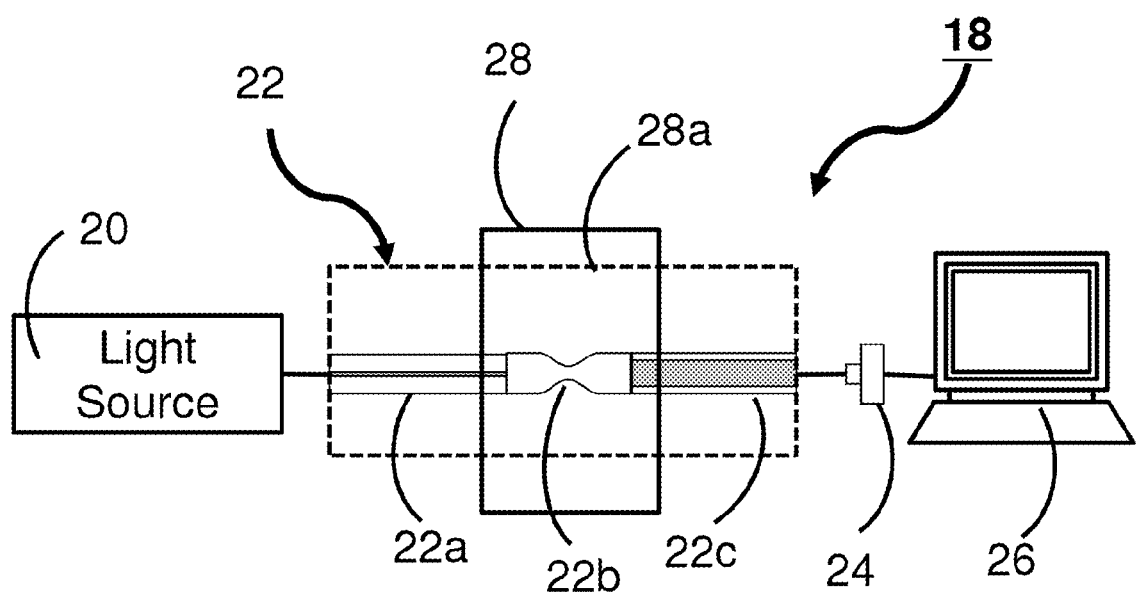
FIG. 1 is a schematic diagram of the optical refractive index measuring system according to one of the embodiment of the present invention.

Now refer to FIG. 1, the first embodiment of the present invention is an optical refractive index measuring system 18, which comprises a coherent light source 20, an assembly fiber 22, a detector 24 and a microcomputer 26. The assembly fiber 22 further comprises a single-mode fiber 22a, an optical fiber sensing module 22b and a multi-mode fiber 22c, wherein the optical fiber sensing module 22b is sandwiched between the single-mode fiber 22a and a multi-mode fiber 22c. The microcomputer 26 at least comprises a microprocessor (not shown) and a computer-readable storage medium or memory (not shown) connected to the microprocessor. The coherent light source 20 is in communication with a first end of the assembly fiber 22 located at the single-mode fiber 22a. The coherent light source 20 is configured to emit coherent light beam to the first end of the assembly fiber 22 and the coherent light beam is directed to the optical fiber sensing module 22b by the single-mode fiber 22a. The optical fiber sensing module 22b is submerged in a liquid analyte 28a when the optical refractive index measuring system 18 is in operation. The coherent light beam further passes through the optical fiber sensing module 22b and the multi-mode fiber 22c, and is captured by a detector 24 which is disposed at a second end of the assembly fiber 22 located at the multi-mode fiber 22c. The detector 24 is further in communication with the microprocessor, which determines the refractive index of the liquid analyte based on the captured light wave/signal.

In another embodiment, the coherent light source 20 is coupled the first end of the assembly fiber 22 located at the single-mode fiber 22a. Coherent light beam at different wavelength can be used in the present invention. In one embodiment, visible coherent light beam can be employed for the present invention. In one specific embodiment, the wavelength of the emitted coherent light beam is 650 nm. The manufacturing cost of the optical refractive index measuring system 18 using visible coherent light beam is cheaper compared to the system using coherent light beam at other wavelength as the detector 24 for capturing visible light is at a lower cost compared to the detector 24 for capturing light at other wavelength. In order to enhance the sensitivity of the optical refractive index measuring system 18, infrared coherent light beam is used. Thus, in another embodiment, the wavelength of the coherent light is 1310 nm or 1550 nm. The wavelength of the coherent light source affects the contrast of the specklegram. In another specific embodiment, the coherent light source 20 is a laser diode and the coherent light beam is a laser beam.

In another embodiment, the detector 24 is disposed near the second end of the assembly fiber 22. In a further embodiment, the detector is disposed 1-10 millimeters apart from the second end of the assembly fiber 22.

In yet another embodiment, the optical refractive index measuring system 18 further comprises a liquid container 28 for containing the liquid analyte 28a.

In order to enhance the sensitivity of the optical refractive index measuring system 18, in one embodiment, the single-mode fiber 22a and the multi-mode fiber 22c are substantially longer than the optical fiber sensing module 22b. In a further embodiment, the single-mode fiber 22a is about 1-2 meters long. In another specific embodiment, the multi-mode fiber 22c is about 1-3 meters long. In yet another specific embodiment, the multi-mode fiber 22c is at least 3 meters long. In another specific embodiment, the multi-mode fiber 22c is fixed and coiled up. It is required that the multi-mode fiber 22c is not deformed after it is fixed and coiled up. In yet another specific embodiment, the optical fiber sensing module 22b is about 1-5 cm.

In yet another specific embodiment, the single-mode fiber 22a is a polarization-maintaining fiber. In another specific embodiment, the detector 24 is an image sensor. In yet another specific embodiment, the detector 24 is a CCD sensor or CMOS sensor.

In one embodiment, the optical fiber sensing module 22c is a no-core fiber. The no-core fiber is an optical fiber having waveguide without cladding. In another specific embodiment, the diameter of the first and second end of the optical fiber sensing module 22b equals to the diameters of the single-mode fiber 22a and the multi-mode fiber 22c respectively. The optical fiber sensing module 22c can be in any shape.

Figure 2:
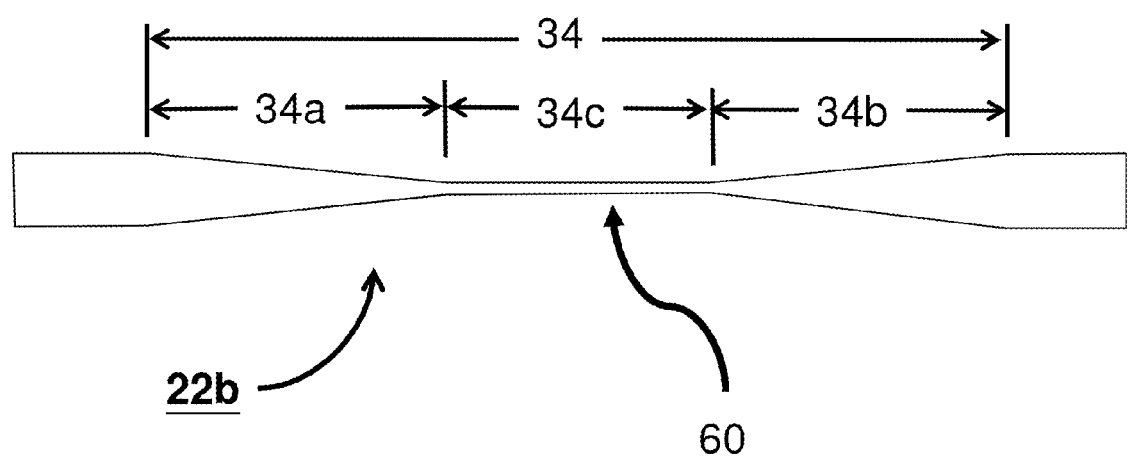
FIG. 2 is the cross-sectional view of the optical fiber sensing module according to different embodiments of the optical fiber sensing module of the present invention.

Referring now to FIG. 2, the cross-sectional view of the optical fiber sensing module 22c according to one specific embodiments of the optical fiber sensing module of the present invention is shown. In order to enhance sensitivity, the optical fiber 22b comprises a biconical fiber taper 34, which further includes a first section 34a, a second section 34b and a third section taper waist 34c. The diameter of the optical fiber sensing module 22b continuously decreases along the longitude axis in the first section 34a while the diameter of the optical fiber sensing module 22b continuously increases along the longitude axis in the second section 34b. The diameter of the third section 34c of the optical fiber sensing module 22b is uniform along the whole third section 34c along its longitude axis. Also, in order to further enhance sensitivity, in another specific embodiment, the optical fiber sensing module 22b is a biconical tapered fiber 60, which comprises biconical fiber taper 34. The diameter of the third section tapered waist 34c can also affect the sensitivity of the sensor. The sensitivity of the sensor increases with the reducing of the diameter of the third section taper waist 34c. In another specific embodiment of the present invention, the diameter of the third section 34c of the biconical fiber taper 34 is ranged from 5 μm to 30 μm. The length of the third section 34c is about 5-20 mm. In another specific embodiment of the present invention, the length of the biconical fiber taper 34 of the fiber optic refractive index sensor is within the range of 10 mm to 30 mm.

Figure 3:
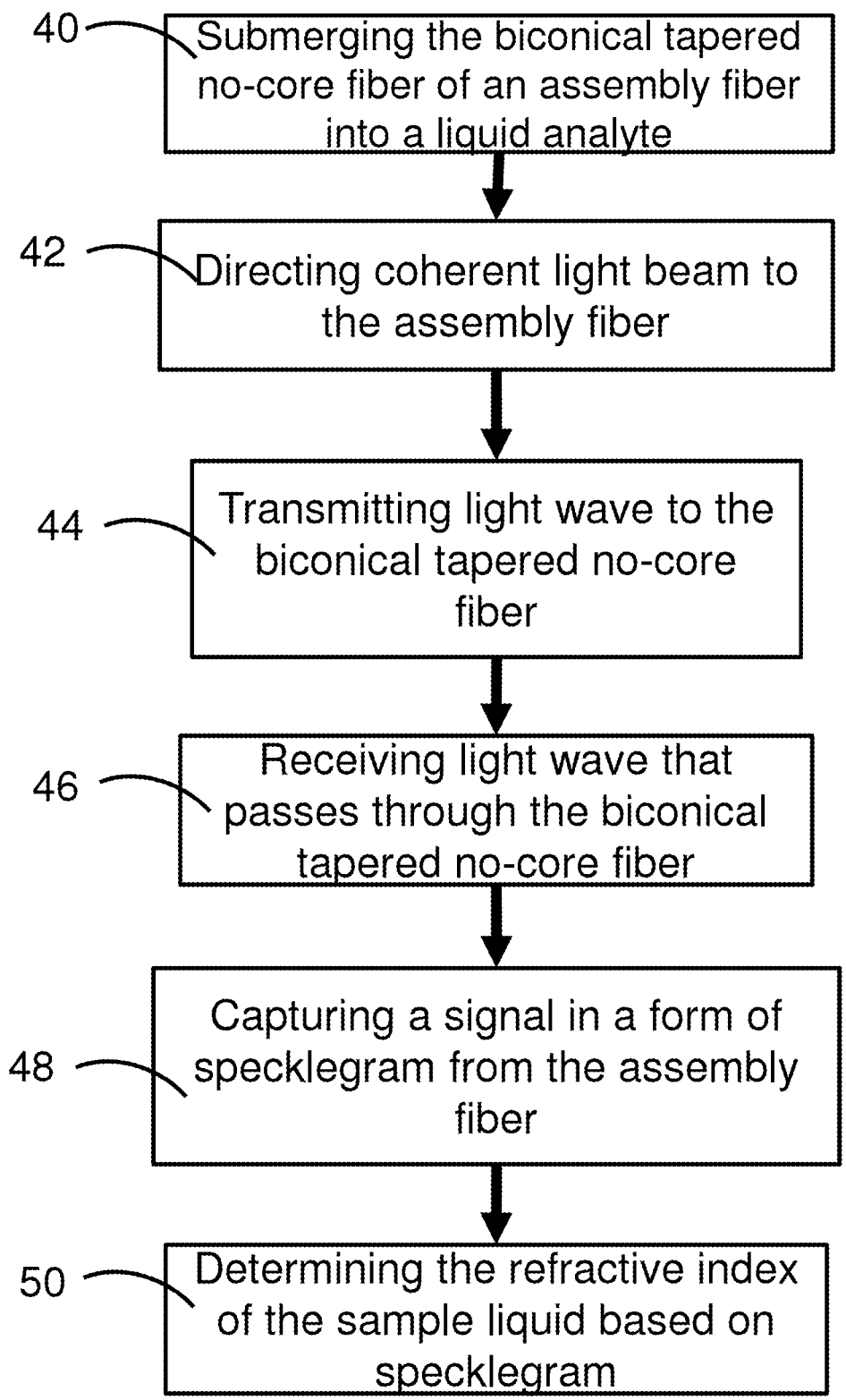
FIG. 3 is the flow chart of a method of detecting vibration according to one of the embodiments of the present invention.

According to another aspect of the present invention, now referring to FIG. 3, a method of measuring refractive index of a liquid analyte is provided. In step 40, the optical fiber sensing module 22b of the assembly fiber 22 is submerged into a liquid analyte, which acts as a cladding of the no-core fiber of the optical fiber sensing module 22b. Then in step 42, a coherent light beam generated by the coherent light source 20 is directed to the first end of the assembly fiber 22. In step 44, the coherent light beam enters the single-mode fiber 22a, which transmits to the optical fiber sensing module 22b with a fixed polarization state. For easier illustration, the mechanism for measuring refractive index of the liquid analyte is discussed based on the case that the optical fiber sensing module 22b is a biconical tapered fiber 60. It will be clear to one skilled in the art that the same mechanism applies to other embodiments of the optical fiber sensing module 22b. When the coherent light enters the optical fiber sensing module 22b, it excites multiple high-order modes in the no-core fiber. Interference between these multiple modes produces the specklegram signal output from the multimode fiber 22c. The specklegram is affected by the refractive index of the liquid surrounding the no-core fiber. The single-mode fiber 22a and no-core fiber 22b are aligned, only $LP_{0m}$ modes are excited in the no-core fiber due to the circular symmetry of the input field when light travels from single-mode fiber 22a to no-core fiber 22b. The excitation coefficient of each mode changes based on the refractive index of the surrounding liquid as the effective refractive index of the cladding of the no-core fiber changes. Thus, plurality of excited modes are generated and these excited modes' phases are different after propagating through the no-core fiber 22b. The excited modes with different phases then propagate along the multi-mode fiber 22c and there is intermodal interference effect at the exit of the multi-mode fiber 22c in step 46. The multi-mode fiber 22c amplifies the phase differences among the excited modes transmitted from the no-core fiber. The light emitted from the multimode fiber 22c (i.e. signal) is then captured by an image sensor 24 in a form of specklegram and the image with speckegram is then digitized for subsequent numerical processing by a microprocessor in step 48. Finally, in step 50, the refractive index of the liquid analyte is determined based on the captured specklegram signal.

Figure 4:
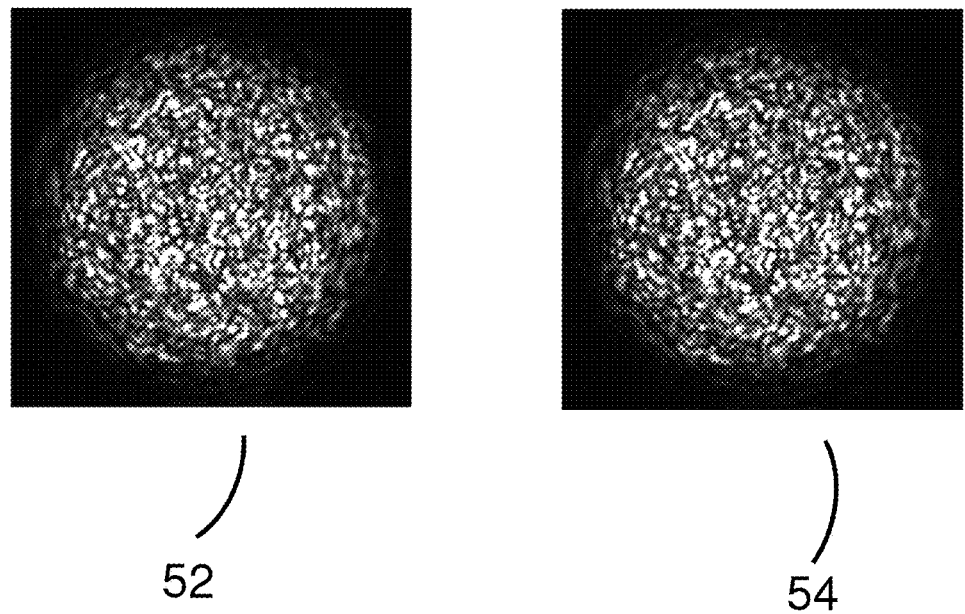
FIG. 4 shows an example of a reference specklegram signal stored in a computer-readable storage medium and a captured specklegram signal.

Referring now to FIG. 4, an example of a reference specklegram signal 54 stored in a computer-readable storage medium and a captured specklegram signal 52 are shown. A reference specklegram signal is stored in a computer-readable storage medium. It was obtained by recording a series of speckegrams at different known refractive indices and picking one of them as the reference specklegram. In one embodiment, a speckegram generated from the lowest refractive index liquid among the series of recorded speckegrams at different known refractive indices is picked as the reference specklegram. The determination of the refractive index of the liquid analyte is based on speckle correlation between the captured specklegram signal 52 and a reference specklegram signal 54 through a correlation function, from which a speckle correlation value r is is obtained. In one embodiment, the correlation function is given as:

$$r = \frac{\sum_m \sum_n (A_{mn} - \overline{A})(B_{mn} - \overline{B})}{\sqrt{\left(\sum_m \sum_n (A_{mn} - \overline{A})^2\right)\left(\sum_m \sum_n (B_{mn} - \overline{B})^2\right)}}$$

Where A is the captured specklegram signal 52 and B is the reference specklegram signal 54 stored in the computer-readable storage medium; m and n are the coordinates of a pixel of the specklegram; $A_{mn}$ and $B_{mn}$ denote the intensity of pixel (m, n) in A and B; and $\overline{A}$ and $\overline{B}$ are the average intensity of all the pixels in A and B. Liquid with different refractive index will generate their unique specklegram. The refractive index of the liquid analyte thereby can be calculated/correlated based on the speckle correlation value r.

Figure 5:
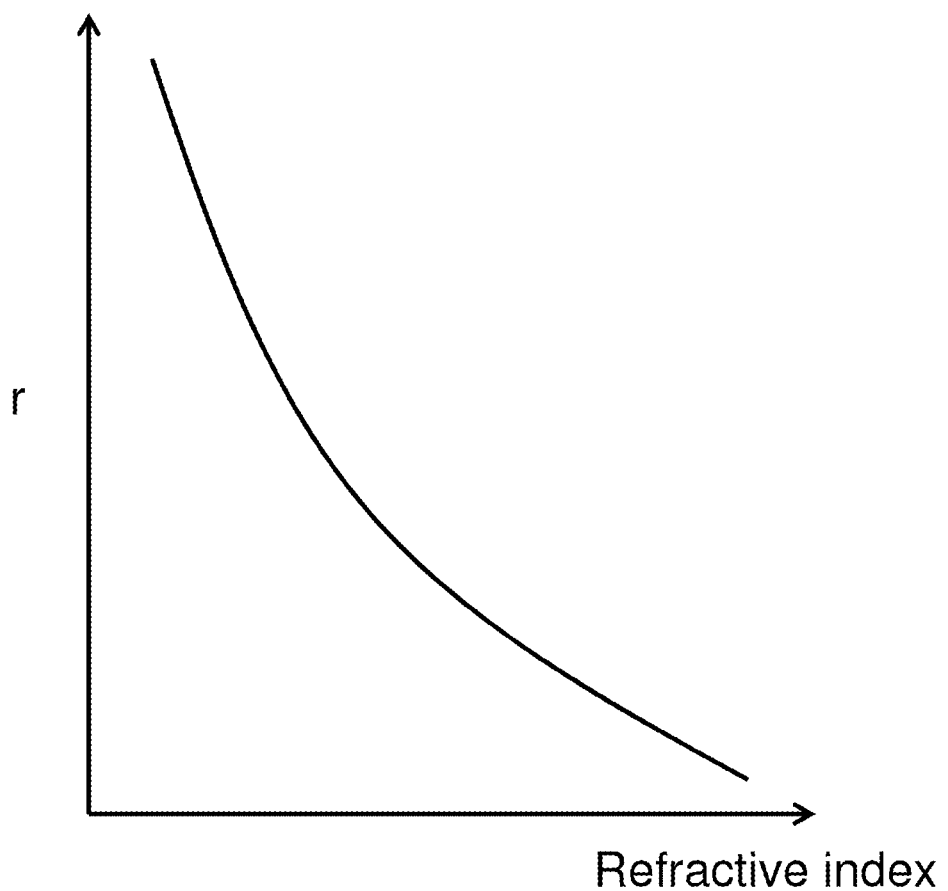
FIG. 5 shows an exemplary graph plotting speckle correlation value against refractive index.

FIG. 5 shows an exemplary graph plotting speckle correlation value r against refractive index. This graph shows a relationship between the speckle correlation value and the refractive index. A plurality of r with known refractive indices is plotted on the graph. After that a curve and a mathematical function correlating the speckle correlation r and the refractive index are obtained by non-linear regression method. In one embodiment, the curve and the mathematical function are obtained using quadratic regression. After obtaining the speckle correlation r by using the correlation function as discussed above, a refractive index can be obtained based on, in one embodiment, the mathematical function of the graph.

The computer storage medium is coupled to the microprocessor and the computer readable storage medium is encoded with computer-readable instructions for causing the microprocessor to execute or operate the steps as mentioned in the systems and the methods above.

According to another aspect of the present invention, a method of manufacturing the optical refractive index measuring system 18 is disclosed. The light transmitting assembly fiber 22 is formed by interconnecting the single-mode fiber 22a, the optical fiber sensing module 22b and the long multi-mode fiber 22c together. In one specific embodiment, the assembly fiber 22 is fabricated just by combining the single-mode fiber 22a, the optical fiber sensing module 22b and the long multi-mode fiber 22c by using a normal fusion splicer. The optical fiber sensing module 22b, as discussed above in some specific embodiment, has a biconical structure. In one specific embodiment, the biconical structure is fabricated by elongating the optical fiber during an arc-discharge provided by a fusion splicer or by etching in hydrofluoric acid.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. An optical detection system for measuring a refractive index of a liquid analyte comprising:
   a light transmitting assembly fiber that includes a single-mode fiber, a no-core optical fiber sensing module and a multi-mode fiber, wherein said no-core optical fiber sensing module is sandwiched between said single-mode fiber and said multi-mode fiber;
   a coherent light source that emits a coherent light beam to a first end of said assembly fiber located at said single-mode fiber;
   a detector that captures a signal from a second end of said assembly fiber located at said multi-mode fiber; and
   a microcomputer programmed to compute a correlation value (r) between said signal and a reference speckleqram signal such that r is computed from:

$$r = \frac{\sum_m \sum_n (A_{mn} - \overline{A})(B_{mn} - \overline{B})}{\sqrt{\left(\sum_m \sum_n (A_{mn} - \overline{A})^2\right)\left(\sum_m \sum_n (B_{mn} - \overline{B})^2\right)}}$$

wherein A is said signal and B is said reference speckleqram signal, m and n are coordinates of a pixel of a speckleqram, $A_{mn}$ and $B_{mn}$ denote intensities of pixel (m, n) in A and B respectively, and $\overline{A}$ and $\overline{B}$ are average intensities of all pixels in A and B; and
   wherein said no-core optical fiber sensing module is submerged into said liquid analyte when said optical detection system is in operation.

2. The optical detection system of claim 1, wherein said no-core optical fiber sensing module is a no-core fiber and further comprises a first section and a second section; a diameter of said no-core optical fiber sensing module being continuously decreasing along a longitude axis in said first section, and continuously increasing along a longitude axis of said second section; and a diameter of a first and second end of said no-core optical fiber sensing module being equal to diameters of said single-mode fiber and said multi-mode fiber respectively.

3. The optical detection system of claim 2, wherein said no-core optical fiber sensing module further comprises a third section, wherein a diameter of said third section is uniform along its longitude axis.

4. The optical detection system of claim 3, wherein said no-core optical fiber sensing module is biconical tapered shaped.

5. The optical detection system of claim 1, wherein said detector is an image sensor.

6. The optical detection system of claim 1, wherein said single-mode fiber is a polarization-maintaining single-mode fiber.

7. The optical detection system of claim 1, wherein said coherent light source is a laser diode and said coherent light beam is a laser beam.

8. The optical detection system of claim 1, wherein said no-core optical fiber sensing module is substantially shorter than said multi-mode fiber.

9. The optical detection system of claim 1, wherein said signal is in a form of a specklegram signal; and said microcomputer further comprising a microprocessor coupled to said detector and a computer-readable storage medium coupled to said microprocessor, said computer-readable storage medium encoded with computer-readable instructions for causing said microprocessor to execute the following step:
obtain said refractive index of said liquid analyte based on said correlation value.

10. A method for measuring a refractive index of a liquid analyte, said method comprising:
providing a light transmitting assembly fiber comprising a no-core optical fiber sensing module, a single-mode fiber and a multi-mode fiber, wherein said no-core optical fiber sensing module is sandwiched between said single-mode fiber and said multi-mode fiber;
submerging said no-core optical fiber sensing module into said liquid analyte;
directing a coherent light beam to a first end of said assembly fiber located at said single-mode fiber by a coherent light source;
generating a signal based on phase differences between excited modes;
capturing said signal at a second end of said assembly fiber located at said multi-mode fiber by a detector; and
determining said refractive index of said liquid analyte based on the captured signal that is in a form of a specklegram signal by analyzing a correlation between said specklegram signal and a reference specklegram signal with a correlation function (r) defined by:

$$r = \frac{\sum_m \sum_n (A_{mn} - \overline{A})(B_{mn} - \overline{B})}{\sqrt{\left(\sum_m \sum_n (A_{mn} - \overline{A})^2\right)\left(\sum_m \sum_n (B_{mn} - \overline{B})^2\right)}}$$

wherein A is said specklegram signal and B is said reference specklegram signal, m and n are coordinates of a pixel of a specklegram, $A_{mn}$ and $B_{mn}$ denote intensities of pixel (m, n) in A and B, and $\overline{A}$ and $\overline{B}$ are average intensities of pixels in A and B.

11. The method according to claim 10, further comprising: directing said coherent light beam from said coherent light source to said no-core optical fiber sensing module with a fixed polarization state through said single-mode fiber.

12. The method according to claim 10, wherein said no-core optical fiber sensing module is a no-core fiber and further comprises a first section, and a second section; a diameter of said no-core optical fiber sensing module being continuously decreasing along a longitude axis in said first section and continuously increasing along a longitude axis of said second section; and a diameter of a first end and second end of said no-core optical fiber sensing module being equal to diameters of said single-mode fiber and said multi-mode fiber respectively.

13. The method according to claim 12, wherein said no-core optical fiber sensing module further comprise a third section, wherein the diameter of said third section is uniform along its longitude axis.

14. The method according to claim 13, wherein said optical fiber sensing module is biconical tapered shaped.

15. The method according to claim 10, further comprising: amplifying said phase differences among said excited modes transmitted from said no-core optical fiber sensing module by said multi-mode fiber.

16. The method according to claim 10, wherein said no-core optical fiber sensing module is substantially shorter than said multi-mode fiber.

17. The method according to claim 10, wherein said detector is an image sensor.

18. A method for measuring a refractive index of a liquid analyte, said method comprising:
providing a no-core optical fiber sensing module shaped with a biconical fiber taper having a first end and an oppositely disposed second end, a polarization-maintaining single-mode fiber connected to the first end of the no-core optical fiber sensing module, and a multi-mode fiber connected to the second end of the no-core optical fiber sensing module such that the no-core optical fiber sensing module is sandwiched between the polarization-maintaining single-mode fiber and the multi-mode fiber;
submerging the no-core optical fiber sensing module into the liquid analyte;
directing a coherent light beam to the polarization-maintaining single-mode fiber that transmits a fixed polarization state to the no-core optical fiber sensing module that excites multiple high-order modes to produce a specklegram output signal from the multi-mode fiber;
capturing the specklegram output signal at an image sensor; and
determining the refractive index of the liquid analyte by analyzing a correlation between the specklegram output signal and a reference specklegram signal through a correlation function from which a correlation function (r) is obtained by:

$$r = \frac{\sum_m \sum_n (A_{mn} - \overline{A})(B_{mn} - \overline{B})}{\sqrt{\left(\sum_m \sum_n (A_{mn} - \overline{A})^2\right)\left(\sum_m \sum_n (B_{mn} - \overline{B})^2\right)}}$$

wherein A is the specklegram output signal and B is the reference specklegram signal, m and n are coordinates of a pixel of the specklegram output signal in a form of a specklegram, $A_{mn}$ and $B_{mn}$ denote intensities of pixel (m, n) in A and B, and $\overline{A}$ and $\overline{B}$ are average intensities of pixels in A and B.

* * * * *